(12) United States Patent
Jossens et al.

(10) Patent No.: US 10,078,061 B2
(45) Date of Patent: Sep. 18, 2018

(54) FLOW-MEASURING DIFFERENTIAL CALORIMETER

(71) Applicants: Commissariat a l'energie atomique et aux energies alternatives, Paris (FR); KEP NUCLEAR, Bagnols sur Ceze (FR)

(72) Inventors: Guillaume Jossens, Villeurbanne (FR); Christophe Mathonat, Lyons (FR); Jean-Charles Hubinois, Dijon (FR); Alain Godot, Darois (FR); Franck Bachelet, Dijon (FR)

(73) Assignees: Commissariat à l'énergie atomique et aux énergies alternatives, Paris (FR); KEP NUCLEAR, Bagnols sur Cèze (FR)

( * ) Notice: Subject to any disclaimer, the term of this patent is extended or adjusted under 35 U.S.C. 154(b) by 248 days.

(21) Appl. No.: 14/760,893

(22) PCT Filed: Jan. 14, 2014

(86) PCT No.: PCT/EP2014/050607
§ 371 (c)(1),
(2) Date: Jul. 14, 2015

(87) PCT Pub. No.: WO2014/111382
PCT Pub. Date: Jul. 24, 2014

(65) Prior Publication Data
US 2016/0025661 A1    Jan. 28, 2016

(30) Foreign Application Priority Data
Jan. 16, 2013 (FR) ...................................... 13 50360

(51) Int. Cl.
*G01K 17/00* (2006.01)
*G01N 25/22* (2006.01)
(Continued)

(52) U.S. Cl.
CPC ............. *G01N 25/22* (2013.01); *G01K 17/00* (2013.01); *G01K 17/04* (2013.01); *G01N 25/4866* (2013.01); *G21C 19/40* (2013.01)

(58) Field of Classification Search
CPC combination set(s) only.
See application file for complete search history.

(56) References Cited

U.S. PATENT DOCUMENTS 6,031,617 A * 2/2000 Berg ..................... G01J 3/0251
356/402
6,572,263 B1   6/2003 Refalo et al.
(Continued)

FOREIGN PATENT DOCUMENTS

| FR | 2 062 446 A1 | 6/1971 |
| FR | 2 516 237 A1 | 5/1983 |
| WO | WO 99/01729 A1 | 1/1999 |

OTHER PUBLICATIONS

French Preliminary Search Report dated Aug. 27, 2013, in Patent Application No. FR 1350360, filed Jan. 16, 2013.
(Continued)

*Primary Examiner* — Lisa Caputo
*Assistant Examiner* — Nasir U Ahmed
(74) *Attorney, Agent, or Firm* — Oblon, McClelland, Maier & Neustadt, L.L.P.

(57) ABSTRACT

A differential calorimeter with flux measurement to measure a heat flux emitted by radioactive materials contained in a container, including: a measurement cell including measurement plates distributed around a container reception containment; and a reference cell including reference plates and a reference sample. The reference plates are placed behind the measurement plates from the container when the container is in the reception containment and the reference sample is under the reception containment.

6 Claims, 3 Drawing Sheets

(51) Int. Cl.
*G21C 19/40* (2006.01)
*G01N 25/48* (2006.01)
*G01K 17/04* (2006.01)

(56) References Cited

U.S. PATENT DOCUMENTS

| | | | |
|---|---|---|---|
| 2010/0135853 A1* | 6/2010 | Broga | G01N 25/48 422/51 |
| 2010/0303124 A1 | 12/2010 | Ellison et al. | |
| 2011/0007775 A1* | 1/2011 | Wu | G01K 17/04 374/11 |
| 2011/0013663 A1* | 1/2011 | Garden | G01N 25/4866 374/11 |
| 2011/0164652 A1* | 7/2011 | ReFalo | G01K 17/00 374/31 |

OTHER PUBLICATIONS

D. S. Bracken, et al. "Application Guide to Safeguards Calorimetry", http://www.lanl.gov/orgs/n/n1/docs/la_13867.pdf, Jan. 1, 2002, XP055076732, pp. 1-66.

S. R. Gunn "Radiometric calorimetry: A review", Nuclear Instruments and Methods, vol. 29, No. 1, Sep. 1964, XP055076749, pp. 1-24.

* cited by examiner

FLOW-MEASURING DIFFERENTIAL CALORIMETER

TECHNICAL FIELD

This invention relates in general to measurement of the thermal power of radioactive materials.

It is a non-destructive and non-intrusive technique for measurement of the thermal power of a sample containing radioactive materials.

It is more particularly applicable to measurement of the thermal power of a sample containing small quantities of radioactive materials distributed non-uniformly in a container that may have a large volume.

STATE OF PRIOR ART calorimetry is a well known technique for quantification of radioelements including Tritium ($^3$H) and Plutonium (Pu) contained in sealed containers.

The main advantages of calorimetry are:
Non-Destructive Assay (NDA),
Non-intrusive assay,
Very good precision,
Accuracy of results,
Possibility of analysing samples with large mass,
Results independent of the matrix type,
No need for sampling and therefore no additional waste,
Results independent of the pressure, the chemical composition, the distribution and presence of non-radioactive materials,
Measurements possible in the liquid, gas or solid phase.

The calorimetry is a very efficient and very precise means for measurement of tritium because tritium is a single Beta emitter with a specific power of 325 mW/g. In this case there is no need to use another measurement means with the calorimetry to determine the precise mass.

For the assay of plutonium, the calorimetry alone is not sufficient to determine the mass of radioelement contained in a sample. This assay technique must be combined with Gamma spectrometry and/or neutron counting to determine the isotopes of the radioelement.

These other two techniques are referenced as measurement means and can be used to determine the composition and mass of the product in a fairly short time without destroying the sample. The main disadvantage of these two techniques is the measurement precision that is between 10 and 20%.

Therefore the advantage of the calorimetry for studying Plutonium is in the precision of this measurement (<1%).

The calorimetry is extremely important for radioactive waste because its measurement precision makes it an essential assay technique for waste producers.

At the present time, waste drums are classified as a function of their activity level (low, medium or high activity). The calorimetry is particularly interesting in the field of low activities so that some waste can be declassified or oriented towards appropriate treatment systems.

Concerning the safety of an installation, storage of waste in a building must not exceed a given activity threshold for nuclear safety reasons. Since calorimetry is a very precise technique capable of measuring the activity of waste with very low uncertainty, it becomes possible to optimise the number of drums in a given building for a given safety level.

Calorimeters usually function in isothermal mode according to the classification produced by W. Hemminger and S. M. Sarge, in the book "Definitions, nomenclature, terms and literature, Hand book of Thermal Analysis and calorimetry, Volume 1, Principles and practice, Series Editor: P. K. Gallagher, Editor: M. E. Brown. Isothermal mode requires that the temperature in the core of the instrument should be kept constant regardless of the heat emitted by the sample.

Different measurement principles can be used:
Heat compensation principle: Determination of the energy necessary to compensate heat released by the sample,
Heat accumulation principle: measurement of the temperature variation provoked by the heat to be measured,
Heat exchange principle: measurement of the temperature difference between the sample and its environment caused by the heat flux to be measured.

There are two major construction principles:
Single measurement system,
Double or differential measurement system.

The principle of measurement by heat compensation consists of globally measuring the modification to the regulation power necessary to keep the calorimeter at a constant temperature when the calorimeter contains an active sample.

The measurement is based on control and quantification of the heat exchange between a thermal block that contains the sample and its environment.

The thermal block is kept at a constant temperature by controlled regulation power. When it does not contain an active sample, the entire heat is added by the regulation. When it does contain an active sample, heat is added both by the thermal regulation and by the sample.

The difference between heat input by the regulation power for the cases without an active sample and with an active sample, is directly related to the power output by the sample (within a calibration factor).

The power is compensated by measuring the temperature of the thermal block at a given point or an average of points and regulating the heating power of the calorimeter relative to this temperature.

The advantage of calorimeters with heat compensation is that the measurement time is shorter than for a calorimeter with measurement of heat flux. Direct thermal contact between the sample and the thermal block (without heat transfer by elements for measurement of the heat flux) facilitates heat exchanges. Therefore the time to stabilise the sample temperature is reduced.

But this measurement technology has three major disadvantages for the study of large volumes and low activity samples:
The large dimensions and characteristics of containers are such that heat fluxes cannot be optimised and therefore it is impossible to obtain a significant saving in the measurement time,
Non-negligible measurement errors may be observed, depending on the location of the source in the container. It is impossible to obtain perfect uniform temperature isotropically,
The measurement precision for low powers and the detection limit depend directly on the regulation precision. It is very difficult to achieve high precision regulation with good stability for the large power ranges necessary to heat large container volumes.

Therefore measurement by compensation is not suitable for a calorimetric study of very large samples with high measurement precision.

Differential measurement with flux measurement is based on the measurement of heat by Peltier elements surrounding the sample in three dimensions. Peltier elements are elements that are sensitive to heat and that create a voltage proportional to the heat flux exchanged between the sample and the thermal block of the calorimeter.

The differential measurement uses a reference cell to eliminate all heat fluxes that will act as parasites to measurement of the sample power. These are disturbances originating from the regulation and external thermal disturbances (for example day/night variation of the room temperature).

The advantage of a differential calorimeter with flux measurement is due to its perfect symmetry and the fact that only the power released by the sample is measured. Therefore the measurement quality does not depend directly on the regulation precision as is the case for a compensation measurement.

Furthermore, since the sample is surrounded by Peltier elements in the three dimensions, heat is measured by a Peltier element regardless of the position of the source. Thus, there is no measurement error depending on the position of the source.

This measurement method is recognised for its precision over a wide measurement range varying from a few microwatts to a few tens of Watts.

However, the differential measurement has the disadvantage that it uses a very large reference cell.

Furthermore, in the case of very large volume containers, it is impossible to be sure that a reference Peltier element will experience the same disturbances as the associated measurement Peltier element. The two Peltier elements have to be more than one meter apart, they are not in contact with the same plates of the thermal block, they are not close to the same heating elements and thermal leaks to the outside close to the two Peltier elements are not perfectly identical. Therefore they do not experience exactly the same heat fluxes and therefore the differential measurement is no longer as efficient as it is on smaller volumes.

Although differential flux measurement has demonstrated its performances, it is not perfectly adapted to the dimensions of very large samples.

PRESENTATION OF THE INVENTION

The invention is aimed at solving problems according to prior art by providing a differential calorimeter with flux measurement to measure a heat flux emitted by radioactive materials contained in a container, comprising:

A measurement cell comprising measurement plates distributed around a container reception containment, A reference cell comprising reference plates and a reference sample, characterised in that The reference plates are placed behind the measurement plates from the container when the container is in the reception containment and in that The reference sample is under the reception containment.

With the invention, it is possible to measure the thermal power of samples containing small quantities of radioactive materials non-uniformly distributed in a container that can have a large volume.

The calorimeter according to the invention satisfies dimensional constraints related to sample volumes that can vary up to several hundred liters. It can be used to measure small quantities with a low uncertainty.

According to one preferred characteristic, the differential calorimeter comprises a fixed part designed to hold the container and a moving part designed to be assembled with the fixed part to form the reception containment.

According to one preferred characteristic, the fixed part of the differential calorimeter contains the reference sample, at least one reference plate and at least one measurement plate.

According to one preferred characteristic, the moving part of the differential calorimeter comprises at least one reference plate and at least one measurement plate.

BRIEF DESCRIPTION OF THE DRAWINGS

Other characteristics and advantages will become clear after reading a preferred embodiment given as a non-limitative example with reference to the figures in which.

DETAILED PRESENTATION OF PARTICULAR EMBODIMENTS

Figure 1:
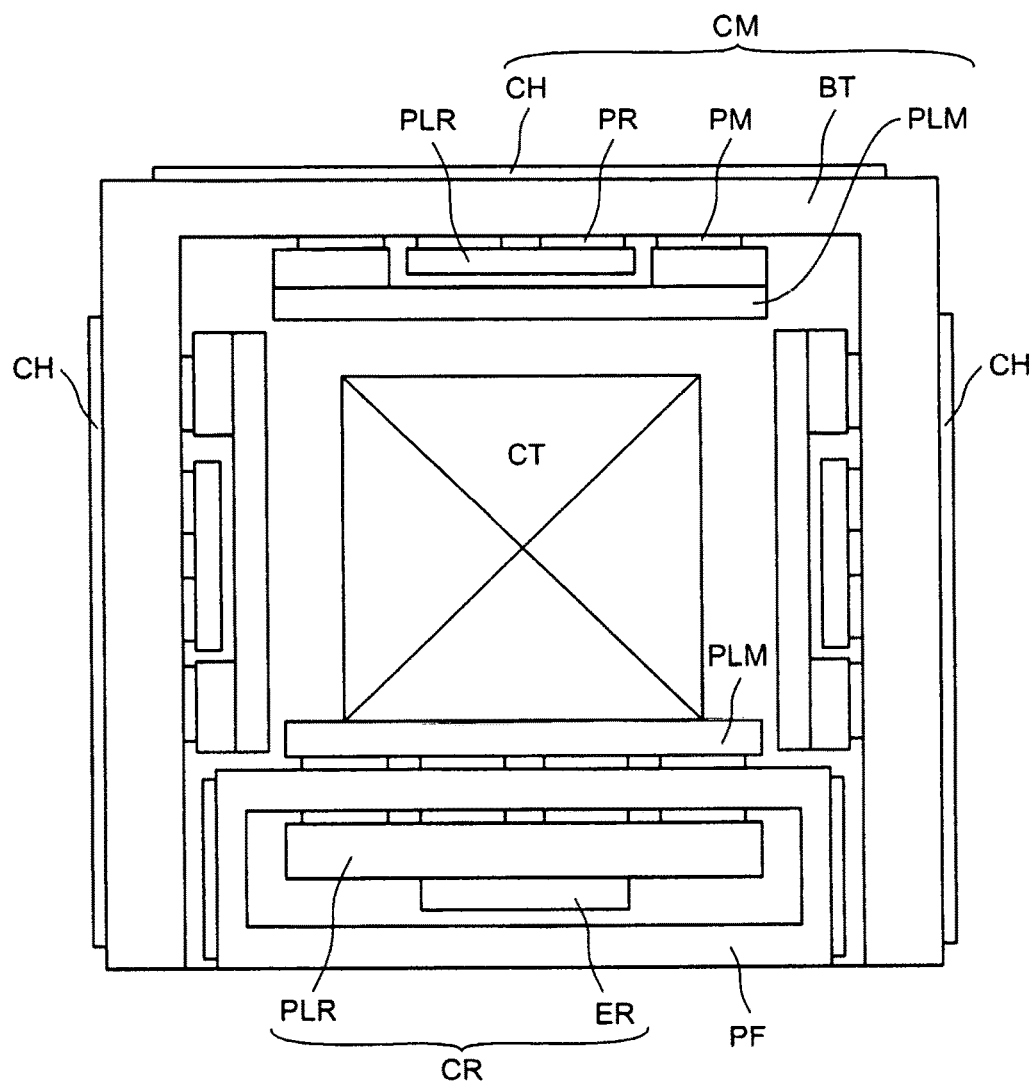
FIG. 1 shows a diagrammatic view of a vertical section through the calorimeter according to this invention.

According to one preferred embodiment described with reference to FIG. 1, the calorimeter comprises a fixed part PF and one or more moving parts PM, that once positioned on the fixed part form a containment to receive a container CT containing radioactive materials for which it is required to measure the heat flux.

The elements of the calorimeter that are particularly interesting in the framework of the invention will be described below.

The calorimeter comprises a measurement cell CM comprising a regulated thermal block BT, reference Peltier elements PR and measurement Peltier elements PM. The measurement cell comprises measurement plates PLM. The measurement cell also comprises heating elements CH and temperature sensors to regulate the thermal block. The thermal block is thus at a stable temperature potential.

The calorimeter comprises a reference cell CR comprising reference plates PLR and a reference sample ER. The reference cell is hidden by the measurement cell.

The lower part of the calorimeter forms the fixed part PF of the calorimeter. It comprises the reference sample ER, on which a reference plate PLR and a measurement plate PLM are mounted.

The container reception containment is located above the fixed part. The containment is surrounded by the moving part PM, for example formed by two half-shells that open up so that the container can be put in position in the containment.

Other structures of the fixed and moving parts are possible as a variant. For example, the fixed part may comprise the base and a side wall, while the moving part may comprise the other three side walls and the top wall.

All the side walls and the top wall of the containment comprise the same elements.

Figure 2:
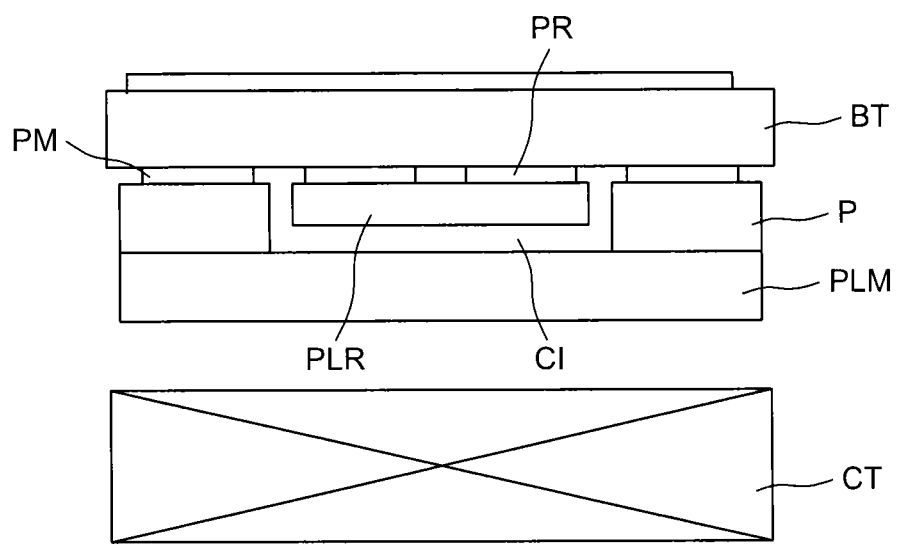
FIG. 2 shows a diagrammatic view of a vertical section through the upper wall of the calorimeter according to this invention.

With reference to FIG. 2, the top wall is separated from the container CT by an air interface. Elements supported by the top wall are described below, starting from the inside and working towards the outside. Starting from this air interface, the top wall comprises a measurement plate PLM that receives heat released by the container by conduction, convection and radiation in air.

The face of the measurement plate PLM that is not facing the container comprises studs P onto each of which measurement Peltier elements PM are fixed. The regulated thermal block BT is fixed to the measurement Peltier elements PM.

The studs P and the measurement Peltier elements PM are around the periphery of the measurement plate PLM. A reference plate PLR is fixed to the reference Peltier elements PR, themselves fixed to the regulated thermal block BT, in a space located between the studs, the measurement plate PLM and the regulated thermal block BT. This reference plate is thus located behind the measurement plate from the container when the container is in the reception containment.

An isolating layer CI separates the measurement plate PLM and the reference plate PLR. Thus, the reference plate PLR is not in direct contact with the container CT. The functions of the reference plate PLR are to:
 simulate the calorific mass of measurement plates,
 be in thermal contact with the regulated block,
 be isolated from heat originating from the container, as much as possible,
 measure heat fluxes due to regulation and disturbances.

Finally, a heating element CH is fixed to the regulated thermal block BT.

The side walls have the same elements as the top wall.

Figure 3:
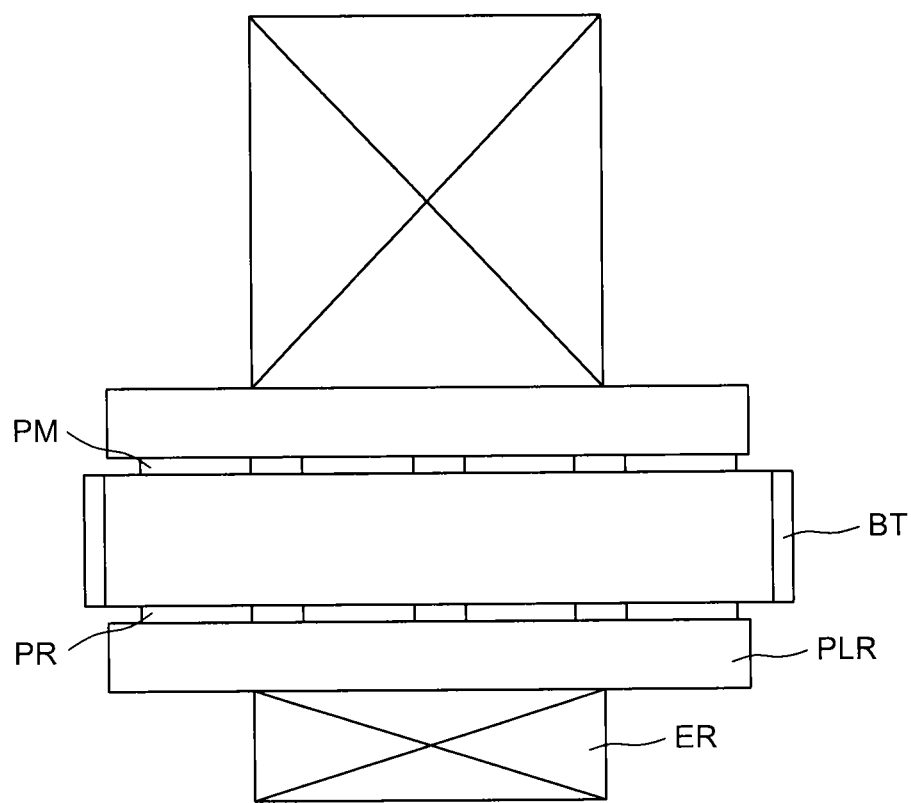
FIG. 3 shows a diagrammatic view of a vertical section through the lower part of the calorimeter according to this invention.

With reference to FIG. 3, the bottom part of the calorimeter comprises a measurement plate PLM on which the container is placed. Therefore, there is contact between the container CT and the measurement plate PLM.

Elements in the bottom part of the calorimeter are described below, from the inside towards the outside. Measurement Peltier elements PM are fixed to the measurement plate PLM.

A regulated thermal block BT is fixed to the measurement Peltier elements PM through one of its faces.

Reference Peltier elements PR are fixed to the regulated thermal block BT on its face opposite the face on which the measurement Peltier elements PM are fixed.

A reference plate PLR is fixed to the reference Peltier elements. This reference plate is thus located behind the measurement plate from the container when the container is in the reception containment.

Finally, a reference sample ER is fixed to the reference plate PLR. The reference sample is thus under the container reception containment.

The opening system is composed of removable half-shells sliding on precision rails. The rails make it possible to open the calorimeter using a secure electro-mechanical system.

Once the two half-shells are separated, the container can easily be placed in the reception containment using a forklift truck.

The size of the calorimeter is appropriate for the size of the containers in which the heat flux is to be measured.

The invention claimed is:

1. A differential calorimeter with flux measurement to measure a heat flux emitted by radioactive materials contained in a container, comprising:
 a measurement cell comprising measurement plates including a first measurement plate on which the container is to be disposed and plural other measurement plates;
 a reference cell comprising reference plates and a reference sample;
 wherein each reference plate is placed facing a side of a respective measurement plate opposite to a side of the respective measurement plate facing the container when the container is disposed on the first measurement plate, and
 wherein the reference sample is under the first measurement plate.

2. A differential calorimeter according to claim 1, further comprising
 a fixed part configured to hold the container and including the first measurement plate and
 a moving part configured to be assembled above the fixed part and configured to open to allow the container to be placed on the fixed part.

3. A differential calorimeter according to claim 2, wherein the fixed part contains the reference sample and at least one reference plate.

4. A differential calorimeter according to claim 2, wherein the moving part comprises at least one reference plate and at least one measurement plate.

5. A differential calorimeter according to claim 1, further comprising Peltier elements affixed onto a side of each of the other measurement plates facing a respective reference plate.

6. A differential calorimeter according to claim 1, wherein each of the other measurement plates faces a different side of the container when the container is disposed on the first measurement plate.

* * * * *